United States Patent [19]

Vergnaud

[11] Patent Number: 5,556,955
[45] Date of Patent: Sep. 17, 1996

[54] PROCESS FOR DETECTION OF NEW POLYMORPHIC LOCI IN A DNA SEQUENCE, NUCLEOTIDE SEQUENCES FORMING HYBRIDIZATION PROBES AND THEIR APPLICATIONS

[75] Inventor: Gilles Vergnaud, Vert le Petit, France

[73] Assignee: Etat Francais represente par le Delegue General pour A'Armement, Paris, France

[21] Appl. No.: 303,004

[22] Filed: Sep. 8, 1994

Related U.S. Application Data

[63] Continuation of Ser. No. 931,311, Aug. 18, 1992, abandoned.

[30] Foreign Application Priority Data

Aug. 22, 1991 [FR] France .................. 91 10516

[51] Int. Cl.$^6$ .............. C07H 21/04; C12N 5/10; C12N 15/63
[52] U.S. Cl. .......... 536/24.31; 536/23.1; 536/24.2; 435/320.1; 435/252.3; 935/6; 935/8
[58] Field of Search .............. 536/23.1, 24.31, 536/24.2; 435/6, 252.3, 320.1; 935/6, 8

[56] References Cited

U.S. PATENT DOCUMENTS 4,963,663  10/1990  White .................. 536/27

FOREIGN PATENT DOCUMENTS

| | | |
|---|---|---|
| 0238329 | 9/1987 | European Pat. Off. . |
| 0390324 | 10/1990 | European Pat. Off. . |
| 2632656 | 12/1989 | France . |
| WO89/07658 | 8/1989 | WIPO . |
| WO91/10748 | 7/1991 | WIPO . |

OTHER PUBLICATIONS

Vergnaud et al. Electrophoresis (Feb. 1991) 12:134–140.
Vergnaud, Nucleic Acids Res. (1989), 17: 7623–7630.
Mamat and Vergnaud, Genomics (Mar. 1992) 12: 454–458.
Lauthier, V. et al., "A synthetic probe, STR 16C2, detects a new polymorphic locus at 5pter (D5S206)," *Nucleic Acids Research*, vol. 19, No. 14, p. 4013.

Jeffreys, A., "Highly variable minisatellites and DNA fingerprints," *Biochemical Society Transactions*, vol. 15, pp. 309–317.

Wong, Z. et al., "Characterization of a panel of highly variable minisatellites cloned from human DNA," *Ann. Hum. Genet.* (1987), 51 269–288.

Nakamura, Y. et al., "New Approach for Isolation of VNTR Markers," *Am. J. Hum. Genet.*, 43:854–859, 1988.

Nakamura, Y. et al., "Variable Number of Tandem Repeat (VNTR) Markers for Human Gene Mapping," *Science*, vol. 235, pp. 1617–1621.

Vergnaud, G. et al., "Detection of single and multiple polymorphic loci by synthetic tandem repeats of short oligonucleotides," *Electrophoresis* 1991, 12, 134–140.

Vergnaud, G., "Polymers of random short oligonucleotides detect polymorphic loci in the human genome," *Nucleic Acids Research*, vol. 17 No. 19 1989, pp. 7623–7630.

Georges, M. et al., "Characterization of a set of variable number of tandem repeat markers conserved in bovidae," *Genomics*, 11, 24–32 (1991).

Jeffreys, A. J. et al., "Hypervariable 'minisatellite' regions in human DNA," *Nature*, vol. 314, Mar. 1985, pp. 67–73.

*Primary Examiner*—W. Gary Jones
*Assistant Examiner*—Carla Myers
*Attorney, Agent, or Firm*—Oliff & Berridge

[57] ABSTRACT

A process for detection of a new polymorphic locus in a DNA sequence is characterized by the following stages. Polynucleotides are prepared by forming an unspecified oligonucleotide including 5 to 10 bases which are repeated 5 to 100 times. A genomic bank is explored by hybridization under low stringency conditions using the prepared polynucleotides which are labelled. The clones that react with the polynucleotides are analyzed by the Southern method. The restriction fragments detected by the polynucleotides are purified and labelled. The genomic DNA of non-consanguineous individuals is analyzed by the Southern method under highly stringent hybridization conditions, with the obtained restriction fragments. The restriction fragments corresponding to new polymorphic loci are selected.

4 Claims, 7 Drawing Sheets

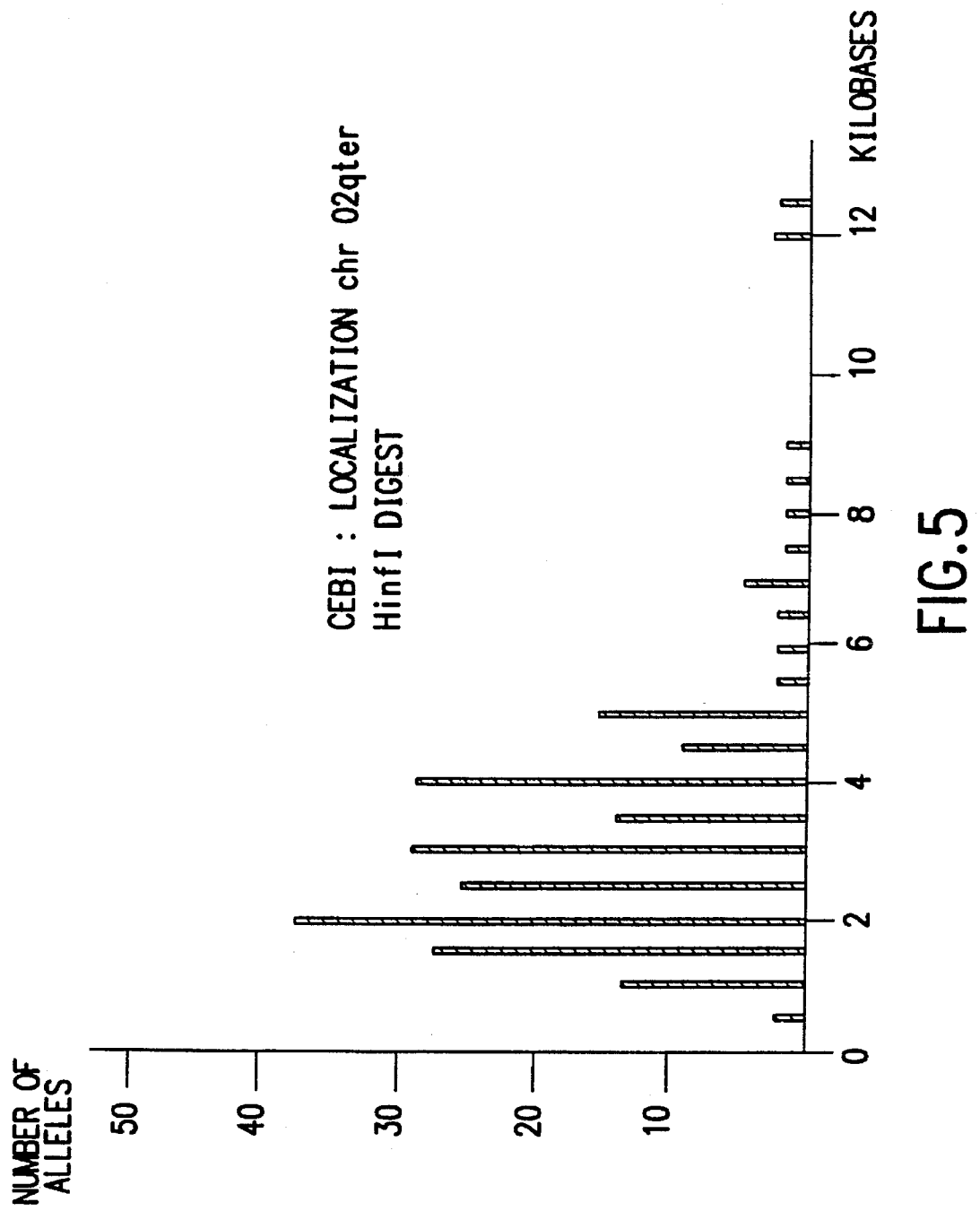

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

AGTCATGGTA GAGC                                14

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

ACGGAGCGGA CGGA                                             14

( 2 ) INFORMATION FOR SEQ ID NO:3:

( i ) SEQUENCE CHARACTERISTICS:
           ( A ) LENGTH: 16 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GTAGAGGTTC TGGACT                                           16

( 2 ) INFORMATION FOR SEQ ID NO:4:

( i ) SEQUENCE CHARACTERISTICS:
           ( A ) LENGTH: 16 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

TTTGAGGTGG ATGGAC                                           16

( 2 ) INFORMATION FOR SEQ ID NO:5:

( i ) SEQUENCE CHARACTERISTICS:
           ( A ) LENGTH: 16 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

AGCTACGGTG TGGACT                                           16

( 2 ) INFORMATION FOR SEQ ID NO:6:

( i ) SEQUENCE CHARACTERISTICS:
           ( A ) LENGTH: 37 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GTTGAGGGGG AGGGAGGGTG GTTGCGGAGG TCCCTGG                     37

( 2 ) INFORMATION FOR SEQ ID NO:7:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

GAGGAGAGGG TGGCGGT                      17

( 2 ) INFORMATION FOR SEQ ID NO:8:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

CTGTGCACCA CCCAGGTCGA ATCTCGGCTC ACTGCGACCT CTGCCTCCGC TAG    53

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GATCGCTCTC TCGA                         14

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

GGCAGGATTG AAGC                         14

( 2 ) INFORMATION FOR SEQ ID NO:11:

( i ) SEQUENCE CHARACTERISTICS:
        ( A ) LENGTH: 14 base pairs
        ( B ) TYPE: nucleic acid ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

AGCTAAGCCT AGCA          14

( 2 ) INFORMATION FOR SEQ ID NO:12:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

AACTGCCCCC TCTT          14

( 2 ) INFORMATION FOR SEQ ID NO:13:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

GACAAACAGA GCAA          14

( 2 ) INFORMATION FOR SEQ ID NO:14:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

CGAGCCAAAC GCTA          14

( 2 ) INFORMATION FOR SEQ ID NO:15:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: DNA (genomic)

(iii) HYPOTHETICAL: NO (iv) ANTI-SENSE: NO (xi) SEQUENCE DESCRIPTION: SEQ ID NO:15:

TCCTAGAATT TTCT                              14

(2) INFORMATION FOR SEQ ID NO:16:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

GGCCGTAGCG CGGT                              14

(2) INFORMATION FOR SEQ ID NO:17:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

ATGCACCGTC GCAC                              14

(2) INFORMATION FOR SEQ ID NO:18:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

GTCAAACGTC TTCC                              14

(2) INFORMATION FOR SEQ ID NO:19:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO ( x i ) SEQUENCE DESCRIPTION: SEQ ID NO:19:

GTTTCTCCAA CAGA 14

( 2 ) INFORMATION FOR SEQ ID NO:20:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:20:

AGCCGTCTGT TTTC 14

( 2 ) INFORMATION FOR SEQ ID NO:21:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:21:

CTGAAAACGA TGGG 14

( 2 ) INFORMATION FOR SEQ ID NO:22:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:

CCGTAGCAGG TAGA 14

( 2 ) INFORMATION FOR SEQ ID NO:23:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

GGTAGAGGCA ACTC 14

( 2 ) INFORMATION FOR SEQ ID NO:24:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

CAAAAGTCAG GCGT                             14

( 2 ) INFORMATION FOR SEQ ID NO:25:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

TGATTTAAGT CCAA                             14

( 2 ) INFORMATION FOR SEQ ID NO:26:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

GGGTGCTCGG GTAC                             14

( 2 ) INFORMATION FOR SEQ ID NO:27:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

CCCCGCTCAG GTAC                             14

( 2 ) INFORMATION FOR SEQ ID NO:28:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:28:

AACAGCTATG ACCATG           16

( 2 ) INFORMATION FOR SEQ ID NO:29:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:29:

ACAATTACGC AGTACT           16

( 2 ) INFORMATION FOR SEQ ID NO:30:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:30:

ACGACACGCC TCCACA           16

( 2 ) INFORMATION FOR SEQ ID NO:31:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:31:

TAAATTTAGA TCGGCA           16

( 2 ) INFORMATION FOR SEQ ID NO:32:

( i ) SEQUENCE CHARACTERISTICS:
        ( A ) LENGTH: 16 base pairs
        ( B ) TYPE: nucleic acid
        ( C ) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:32:

AGAACCAGGC TCAGGG 16

(2) INFORMATION FOR SEQ ID NO:33:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:33:

GTAGACGTTC TGCACT 16

(2) INFORMATION FOR SEQ ID NO:34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:34:

GTAGTGGTCC TGGACT 16

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:35:

GTAGAGCTTC TGCAGT 16

(2) INFORMATION FOR SEQ ID NO:36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:36:

GGAGAGGTTG TGGACT 16

(2) INFORMATION FOR SEQ ID NO:37:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:37:

GTAGAGGGGC TGGACT 16

(2) INFORMATION FOR SEQ ID NO:38:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:38:

GTAGAGGTTG GGGACG 16

PROCESS FOR DETECTION OF NEW POLYMORPHIC LOCI IN A DNA SEQUENCE, NUCLEOTIDE SEQUENCES FORMING HYBRIDIZATION PROBES AND THEIR APPLICATIONS

This is a continuation of application Ser. No. 07/931,311 filed Aug. 18, 1992, now abandoned.

The invention concerns a process for detection of polymorphic loci in a human or animal genome DNA sequence. The invention also concerns nucleotide sequences forming probes for identification by hybridization of polymorphic loci contained in an DNA sample.

In many circumstances it is extremely important to determine the identity of an individual, for example to determine consanguinity between two persons or, in the course of a police investigation, to collect evidence concerning the guilt of an individual. It could also be important to determine the pedigree of an animal or the genetic identity of a cellular line of descent.

Recently human and animal genomes have been found to contain loci with a variable number of tandem repeats called VNTRs or polymorphic loci or minisatellite regions. These polymorphic loci consist of short DNA sequences repeated in tandem, for a number of times which can vary greatly from one individual to another (JEFFREYS A. J. et al, Nature (1985), 314, p. 67–73). The elements repeated in tandem are not necessarily perfectly identical. These sequences repeated and distributed over the genome have the particularity of being transmitted by an individual to his descendants.

Polymorphic loci thus form a genetic print of the individual which is highly useful for his identification from a DNA sample.

Research to date has revealed 200 polylmorphic loci in the human genome out of the estimated 1500 thought to exist in man, and has helped to prepare hybridization probes for the analysis of human DNA.

Hybridization of such a probe, suitably marked, with a sample of DNA, fragmented and separated by electrophoresis, is used to obtain hybridization images of the probe with the complementary portions of DNA present in the sample.

Comparison of the position, number and size of the bands produced by analysis of DNA from two distinct samples, allows determining if these samples come from the genome of the same individual or from the genomes of different individuals who are consanguineous or non-consanguineous.

Such probes have been described, notably in the French patent registration request made out in the name of IMPERIAL CHEMICAL INDUSTRIES PLC published under No. 2 632 656 as well as the European patent registration request in the name of IMPERIAL CHEMICAL INDUSTRIES published under No. 238 329.

In order to increase the reliability of these DNA analyses, it is necessary to have a large number of probes. Now, the procedures implemented to identify new polymorphic loci and prepare the corresponding probes are based on the screening of genomic banks and are not satisfactory since some have the drawback of using minisatellite regions which are already known and others often require prior richening in minisatellite structures by selection of the size of the screened fragments.

This invention is specifically meant to provide a method for isolating new polymorphic loci in animal and human genomes and to prepare hybridization probes for detection of unknown polymorphic DNA sequences bearing the abovementioned polymorphic loci without the disadvantages arming from earlier techniques.

The research by inventors in the field of synthetic probes each consisting of a polymer formed from tandem repeats of an oligonucleotide, have allowed them to find a new process for isolating new polymorphic loci in a genomic DNA sequence and to prepare hybridization probes for identification of unknown polymorphic DNA sequences containing the abovementioned polymorphic loci.

BRIEF DESCRIPTION OF THE DRAWINGS

FIG. 5 shows the distribution in size of the HinfI alleles observed with the CEB1 fragment;

Figure 1:
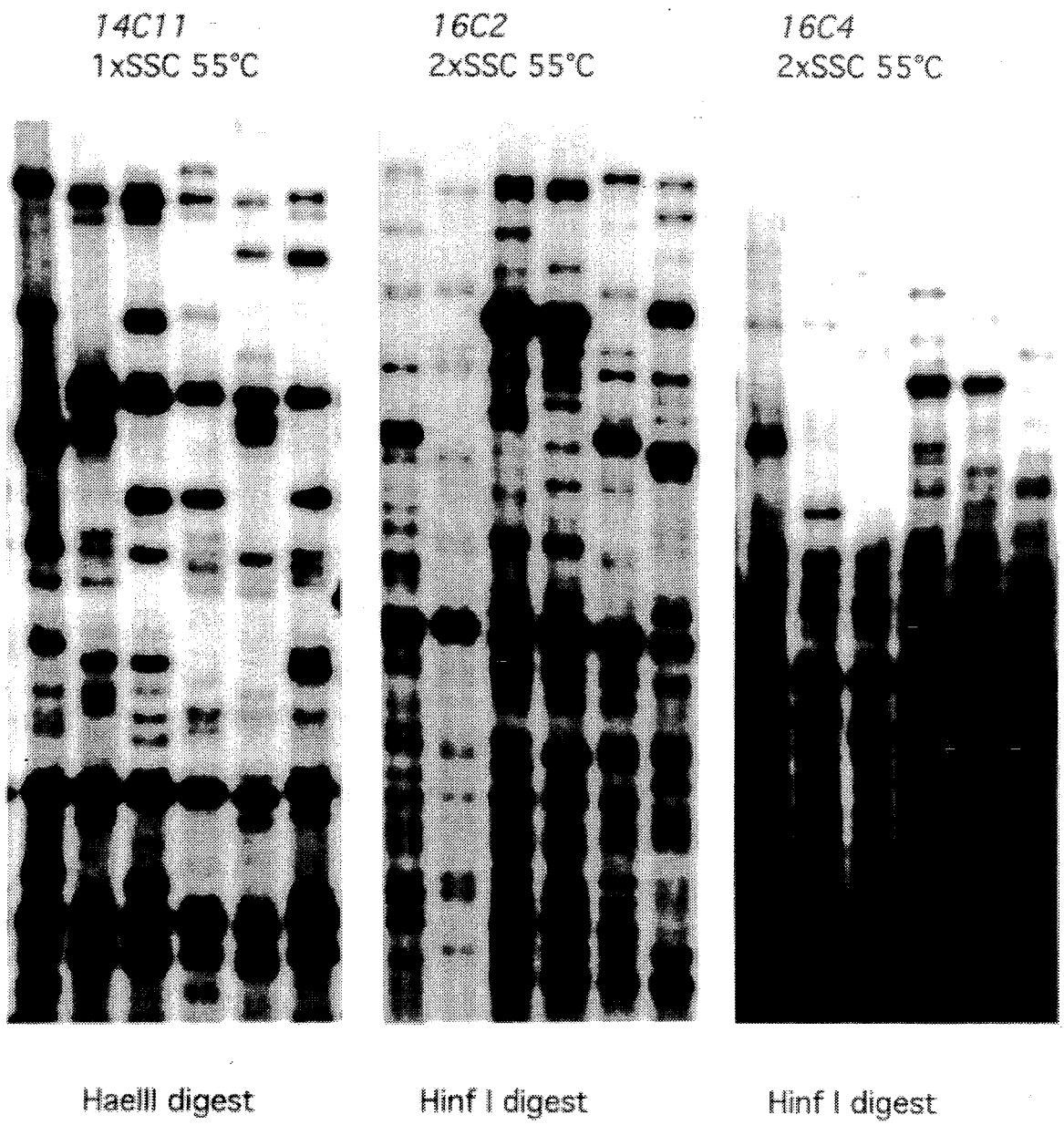
FIG. 1 shows the hybridization profile obtained with 6 non-consanguineous individuals using polynucleotides 14C11, 16C2 and 16C4.

The invented process for detection of new polymorphic loci in a DNA sequence is characterized by the following steps:

a - Preparation of polynucleotides, each consisting of an undetermined oligonucleotide containing 5 to 20 bases and repeated from 4 to 200 times.

b - Exploration of a genomic bank by hybridization under slightly stringent conditions with the polynucleotides prepared in (a) and marked;

c - Analysis by Southern's method of clones which have reacted with the polynucleotides;

d - Purification and, if necessary, marking of the restriction fragments detected by the polynucleotides;

e - Analysis by the Southern method of the genomic DNA of non-consanguineous individuals which has reacted under highly stringent hybridization conditions with the restriction fragments obtained under (d) and selection of the restriction fragments corresponding to new polymorphic loci.

In a form preferred by the invention, step (b) consists of exploring a bank of human cosmids.

The invention process allows efficient detection of new polymorphic DNA sequences bearing polymorphic loci. The process is easily implemented using polynucleotide preparations each formed by tandem repeats of any oligonucleotide.

At step (a) polynucleotides are advantageously formed, each from any oligonucleotide, including 10 to 18 bases repeated 10 to 60 times.

The polynucleotides used in the invention process have the following formulae:

(AGTCATGGTAGAGC) n (SEQ ID No. 1)

(ACGGAGCGGACGGA) n (SEQ ID No. 2)

(GTAGAGGFTCTGGACT) n (SEQ ID No. 3)

(TIFGAGGTGGATGGAC) n (SEQ ID No. 4)

(AGCTACGGTGTGGACT) n (SEQ ID No. 5)

in which n is higher than 20.

After marking, these polynucleotides are used to explore the bank of cosmids and show up, by hybridization under the low stringency conditions defined below, cosmids containing polymorphic DNA sequences.

Low stringency hybridization conditions for the exploration of the cosmid bank can be, for example, defined as follows:

hybridization at 50° C., 0.9M Na+ions washing at 55° C., 0.15M Na+ions

These hybridization conditions allow pairing of about 50% of the polynucleotides with the cosmid target.

The polynucleotides used in the invention process are labeled using any conventional labeled.

They can be labeled using a radioactive tracer such as $32_P$, $35_S$, $125_I$, $3_H$ or $14_C$. The radioactive marking can be done by any professionally known method.

The polynucleotides can also be labeled at (3') by addition of one or several deoxyribonucleotides or ribonucleotides or a nucleotide analogue such as a dideoxynucleotide labeled in the alpha position by $^{32}P$, in the presence of the deoxynucleotidyl terminal transferase. The polynucleotides can also be labeled at (5') using a kinase, for example the T4 polynucleotide kinase. In this case the labeling consists of a transfer onto the polynucleotides of radioactive phosphate of a nucleotide labeled in the gamma position. The polynucleotides can also be labeled at each end by the addition of any radioactively labeled sequence in the presence of a ligase.

They can also be labeled by random priming or also, during their chemical synthesis, incorporate one or several radioactive ribonucleotides or deoxyribonucleotides.

The hybridization detection method will depend on the radioactive label used and can be based on autoradiography, liquid scintillation, gamma radiation count or any other technique allowing the detection of radiation emitted by the radioactive label.

A non-radioactive label can also be used by associating with the polynucleotides, groups with immunological properties such as an antigen or a hapten, a specific affinity for some reagents such as a ligand, properties allowing for completion of enzymatic reactions such as an enzyme or an enzyme substrate. The polynucleotides can be labeled by random priming or during chemical synthesis by incorporating one of several ribonucleotides or deoxyribonucleotides labeled by non-radioactive methods. Non-radioactive labeling can also be done by incorporation at one end (3') of one or several deoxyribonucleotides or ribonucleotides or a nucleotide analogue such as dideoxynucleotide including one of these groups. The labeling can also be done directly by chemical modification of the oligonucleotide such as photobiotinylation or sulfonation. It can also be done by addition at (3') or (5') of tracer molecules by chemical reaction after synthesis. The polynucleotides can also be labeled at each end by addition of any sequence containing tracer molecules in the presence of a ligase. The method for detection and revelation of the hybridization will depend on the non-radioactive label used.

After exploration of the cosmid bank, analysis by the Southern method of the clones which have reacted to the polynucleotides leads to restriction fragments which, after purification, form nucleotide sequences which can be suitably labeled in view of Southern blot analysis of the genomic DNA of non-consanguineous individuals. This Southern blot analysis leads to detection by hybridization of new polymorphic loci, under the highly stringent conditions defined below.

High-stringency hybridization conditions for Southern blot exploration of genomic DNA of non-consanguineous individuals can be, for example, defined as follows:

Hybridization at 65 or 70° C., 0.9M ions Na+.

Washing at 65° C., 0.015 or 0.15M ions Na+

This invention also concerns nucleotide sequences for identification by hybridization of polymorphic loci detected by the process described above.

The nucleotide sequences forming the restriction fragments which have allowed detection and isolation of new polymorphic loci according to the invention process can be used advantageously as hybridization probes for the identification of these new polymorphic loci.

A first nucleotide sequence for identification of a polymorphic locus by hybridization, detected by the invention process using a polynucleotide with the formula (AGT-CATGGTAGAGC)$_n$ (SEQ ID No. 1), where n is higher than 20, corresponds to restriction fragment AluI with about 3.8 kb of cosmid, containing the portion of human genomic DNA located at position 6q27 with 97% of heterozygosity. This cosmid was cloned in the pWE15 vector, inserted in *Echerichia. Coli* and deposited at the French "Collection Nationale des Cultures de Micro-organismes" (National Collection of Micro-organism Cultures) (CNCM) at the Pasteur Institute 25 rue dy Docteur Roux, 75724 Paris Cedep 15 on Aug. 14, 1991, under reference 1–11134. This first sequence will be referred to in the following experimental description as "CEB4".

A second nucleotide sequence for identification of a polymorphic locus by hybridization, detected by the invention process using a polynucleotide with the formula (ACG-GAGCGGACGGA)$_n$ (SEQ ID No. 2), where n is higher than 20, corresponds to the restriction fragment of about 4 kb obtained after hydrolysis by AluI and HaeILI of the cosmid containing the portion of human genomic DNA located at position 7 q with 97% of heterozygosity. This cosmid was cloned in the pWE15 vector, inserted in *Echerichia. Coli* and deposited at the CNCM on Aug. 14, 1991, under reference I-1135. This second sequence will be referred to in the following experimental description as "CEB13".

A third nucleotide sequence for identification of a polymorphic locus by hybridization, detected by the invention process using a polynucleotide with the formula (ACG-GAGCGGACGGA)$_n$, (SEQ ID No. 2), where n is higher than 20, corresponds to the restriction fragment of about 3.8 kb obtained after hydrolysis by HaeIII and HinfI of the cosmid containing the portion of human genomic DNA located at position 1 p with 98% of heterozygosity. This cosmid was cloned in the pWE15 vector, inserted in *Echerichia. Coli* and deposited at the CNCM on Aug. 14, 1991, under reference I-1136. This third sequence will be referred to in the following experimental description as "CEB15".

A fourth nucleotide sequence for identification of a polymorphic locus by hybridization, detected by the invention process using a polynucleotide with the formula (GTAGAG-GTTCTGGACT)$_n$, where n is higher than 20, consists of the following unitary motif:

5'GTIGAGGGGGAGGGAGGGTGGTFGCG-GAGGTCCCTGG 3' (SEQ ID No. 6)

with about 100 tandem repeats.

The above nucleotide sequence will be referred to as CEB1 in the following experimental description. It corresponds to restriction fragment AluI of the cosmid containing the portion of human genomic DNA located at position 2q37.3 with 93% of heterozygosity. This cosmid was cloned in the pWE15 vector and inserted in *Echerichia. Coli.*

A fifth nucleotide sequence for identification of a polymorphic locus by hybridization, detected by the invention process using a polynucleotide with the formula (GTAGAG- GTYCTGGACT)$_n$ (SEQ ID No. 3), where n is higher than 20, consists of the following unitary motif:

5'GAGGAGAGGGTGGCGGT 3' (SEQ ID No. 7)

with about 400 tandem repeats.

The above nucleotide sequence will be referred to as CEB2 in the following experimental description. It corresponds to restriction fragment HinfI of about 6 kb of the cosmid containing the portion of human genomic DNA located at position 20q13.1 with 57% of heterozygosity. This cosmid was cloned in the pWE15 vector and inserted in *Echerichia. Coli.*

A sixth nucleotide sequence for identification of a polymorphic locus by hybridization, detected by the invention process using a polynucleotide with the formula (GTAGAG-GITCTGGACT)$_n$ (SEQ ID No. 3), where n is higher than 20, corresponds to the restriction fragment of about 2.5 kb obtained after hydrolysis by HaeIII and HinfI of the cosmid containing the portion of human genomic DNA located at position 6q27 with 95% of heterozygosity. This cosmid was cloned in the pWE15 vector, inserted in *Echerichia. Coli* and deposited at the CNCM on Aug. 14, 1991, under reference I-1133. This sixth sequence will be referred to in the following experimental description as "CEB3".

A seventh nucleotide sequence for identification of a polymorphic locus by hybridization, detected by the invention process using a polynucleotide with the formula (GTA-GAGGTTCTGGACT)$_n$ (SEQ ID No. 3), where n is higher than 20, consists of the following unitary motif:

5'CTGTGCACCACCCAGGTCGAATCTCG-
GCTCACTGCGACCTC TGCCTOCGCGTAG
3'(SEQ ID NO. 8)

with about 50 tandem repeats.

The above nucleotide sequence will be referred to as CEB5 in the following experimental description. It corresponds to restriction fragment HaeIII of about 3 kb of the cosmid containing the portion of human genomic DNA located at position 13q34.1 with 80% of heterozygosity. This cosmid was cloned in the pWE15 vector and inserted in *Echerichia. Coil.*

The nucleotide sequences can be labeled by any conventional label used for the purpose as stated above for the polynucleotides.

The invention also naturally includes the polynucleotides and nucleotide sequences complementary to the previous ones and thus capable of being paired with the same portion of DNA because of its bicaternary structure.

Also included in the invention are the polynucleotides and sequences of nucleotides in which the thymines are replaced by uracils and in which one of the four bases is replaced by an inosine.

The invention also concerns all polynucleotides and sequences of nucleotides only distinguished from the previous ones on the level of their sequence by addition and/or suppression and/or substitution of one or more nucleotides insofar as these do not modify the hybridization properties of the said polynucleotides or sequences of nucleotides.

The invention also concerns a process for genetic amplification of a polymorphic locus detected by the invention process. This amplification process consists in fixing by hybridization to the ends of the said polymorphic locus, a priming sequence of 17 to 30 bases, suitably selected from all or part of the sequences on either side of the polymorphic loci, obtained from cosmids, then performing an enzymatic extension process using DNA-polymerase, followed by a denaturing process, and repeating the hybridization-extension-denaturing cycle, known as PCR as described by CETUS, a sufficient number of times to increase the quantity of the original polymorphic locus sequence exponentially with respect to the number of cycles performed.

The invention also includes a process for identification of a polymorphtic locus detected by the process in conformity with the invention, which consists of placing a denatured DNA sequence fixed on a support in contact with a sequence of nucleotides according to the invention, labeled and forming a probe, in a milieu and under conditions allowing hybridization, then detection of the hybrids produced and measurement of the quantities and locations of the labeled probe on the DNA sequence being studied.

The invention finally consists of the use of nucleotide sequences according to the invention, labeled if necessary, in procedures for diagnosis of hereditary or tumor producing illnesses.

Among these we could mention the research on the loss of alleles or of chromosome areas in tumors or the identification of tumor areas using polymorphic probes with high mutation rates.

Besides the above characteristics, the invention includes other details which will become clear in the following description and which refer to examples of execution of the invention process. It is to be understood, however, that these examples do not in any way limit the scope of the claims.

I - MATERIALS AND METHODS

1) Preparation of polynucleotides

The polynucleotides were prepared according to the method described by VERGNAUD et al. in Electrophoresis, 1991, 12, 134–140. They consist of polymers formed from synthetic oligonucleotides with tandem repeats of undetermined sequences. The oligonucleotides listed in Table 1 below have been prepared and polymerized to obtain polynucleotides of a few hundreds of bases.

TABLE 1

| Polynucleotide | Sequence | % G + C | Washing |
| --- | --- | --- | --- |
| 14C1 | GATCGCTCTCTCGA (SEQ ID NO. 9) | 57% | 4XSSC 60° C. |
| 14C2 | GGCAGGATTGAACGC (SEQ ID NO. 10) | 57% | 2XSSC 57° C. |
| 14C3 | AGCTAAGCCTAGCA (SEQ ID NO. 11) | 50% | 1XSCC 55° C. |
| 14C4 | AACTGCCCCCTCTT (SEQ ID NO. 12) | 57% | 3XSSC 63° C. |
| 14C5 | GACAAACAGAGCAA (SEQ ID NO. 13) | 43% | 1XSSC 55° C. |
| 14C5 | CGAGCCAAACGCTA (SEQ ID NO. 14) | 57% | 1XSSC 50° C. |
| 14C7 | TCCTAGAATTTTCT (SEQ ID NO. 15) | 29% | 3XSSC 45° C. |
| 14C8 | GGCCGTAGCGCGGT (SEQ ID NO. 16) | 79% | 1XSSC 60° C. |
| 14C9 | ATGCACCGTCGCA (SEQ ID NO. 17) | 64% | 1XSSC 60° C. |
| 14C10 | GTCAAACGTCTTCC (SEQ ID NO 18) | 50% | 3XSSC 45° C. |
| 14C11 | AGTCATGGTAGAGC (SEQ ID NO. 1) | 50% | 1XSSC 55° C. |
| 14C12 | GTTTCTCCAACAGA (SEQ ID NO. 19) | 43% | 1XSSC 50° C. |
| 14C13 | AGCCGTCTGTTTTC (SEQ ID NO. 20) | 50% | 1XSSC 50° C. |

TABLE 1-continued

| Polynucleotide | Sequence | % G + C | Washing |
|---|---|---|---|
| 14C14 | CTGAAAACGATGGG (SEQ ID NO. 21) | 50% | 1XSSC 55° C. |
| 14C15 | CCGTAGCAGGTAGA (SEQ ID NO. 22) | 57% | 1XSSC 50° C. |
| 14C16 | GGTAGAGGCAACTC (SEQ ID NO. 23) | 57% | 3XSSC 57° C. |
| 14C17 | CAAAAGTCAGGCGT (SEQ ID NO. 24) | 50% | 1XSSC 55° C. |
| 14C18 | TGATTTAAGTCCAA (SEQ ID NO. 25) | 29% | 3XSSC 45° C. |
| 14C19 | GGGTGCTCGGGTAC (SEQ ID NO. 26) | 71% | 1XSSC 50° C. |
| 14C20 | CCCCGCTCAGGTAC (SEQ ID NO. 27) | 71% | 3XSSC 55° C. |
| 14C21 | ACGGAGCGGACGGA (SEQ ID NO. 2) | 71% | 1XSSC 55° C. |
| 16C1 | AACAGCTATGACCATG (SEQ ID NO. 28) | 44% | 3XSSC 57° C. |
| 16C2 | GTAGAGGTTCTGGACT (SEQ ID NO. 3) | 50% | 2XSSC 55° C. |
| 16C3 | ACAATTACGCAGTACT (SEQ ID NO. 29) | 50% | 2XSSC 60° C. |
| 16C4 | TTTGAGGTGGATGGAC (SEQ ID NO. 4) | 50% | 2XSSC 60°0 C. |
| 16C5 | ACGACACGCCTCCACA (SEQ ID NO. 30) | 62% | 2XSSC 65° C. |
| 16C6 | TAAATTTAGATCGGCA (SEQ ID NO. 31) | 31% | 2XSSC 60° C. |
| 16C17 | AGACCAGGCTCAGGG (SEQ ID NO. 32) | 63% | 2XSSC 55° C. |
| 16C18 | GTAGAcGTTCTGcACT (SEQ ID NO. 33) | 50% | 2XSSC 55° C. |
| 16C19 | GTAGtGGTcCTGGACT (SEQ ID NO. 34) | 56% | EXSSC 55° C. |
| 16C20 | GTAGAGcTTCTGcAgT (SEQ ID NO. 35) | 50% | EXSSC 55° C. |
| 16C21 | GgAGAGGTTgTGGACT (SEQ ID NO. 36) | 56% | 2XSSC 55° C. |
| 16C22 | GTAGAGGggCTGGACT (SEQ ID NO. 37) | 63% | EXSSC 55° C. |
| 16C23 | GTAGAGGTTggGGACg (SEQ ID NO. 38) | 63% | 2XSSC 55° C. |
| 16C27 | AGCTACGGTGTGGACT (SEQ ID NO. 5) | 56% | 1XSSC 55° C. |

2) Exploration of a human cosmid bank

A human cosmid bank supplied by STRAGENE CLONING SYSTEM (Reference 951202, male, placenta, in the pWE15 plasmid vector) has been used as recommended by the supplier, with membranes of the GeneScreen NEN type.

About 300,000 cosmids were explored with polynucleotides 14C11, 14C21, 16C2, 16C4 and 16C27. For this, the filters were hybridized using the abovementioned probes in a buffer solution containing: 2% SDS, 0.45M Na2PO4, pH 7.2, 0.5% powdered milk, 1 nM EDTA, one night at a temperature of 50° C. and washed twice at least 30 minutes in the conditions mentioned in Table 1 (1×SSC=0.15M NaCl, 15 nM sodium citrate).

3) Identification of the polymorphic DNA sequences

The cosmid DNA was prepared according to conventional protocols (SAMBROOK et al. 1989), digested with common restriction enzymes supplied by APPLIGENE, such as: AluI, HaeIII, Sau3A, HinfI, and used according to the manufacturer's recommendations, then subjected to electrophoresis with Southern blot analysis, according to the method described by Sambrook et al. (1989). The restriction fragments previously detected at the cosmids by hybridization under low stringency conditions, using polynucleotides 14C11, 14C21, 16C2, 16C4 or 16C27 are identified by hybridization under similar conditions and the corresponding DNA, called CEB, is then purified by electroelution and labeled by random priming, according to the method described by FEINBER and VOGELSTEIN (1983) using dCTP (32P).

In some cases, the whole cosmid can be used as a probe after neutralization of the repetitive DNA sequences as described by BIONDEN et al. (1989).

4) Hybridization by Southern blot transfer

Hybridizations by Southern blot transfer were performed according to the method described by VERGNAUD et al. in Electrophoresis (1991) 12, 134–140. A probe concentration between 0.1 and 0.2 million dpm/ml is sufficient. The membranes were exposed with two amplifier screens and an XAR5 Kodak type film for 1 to 4 nights at −80° C.

5) Sequencing

The sequencing was done according to the "dideoxy chain termination" method presented by SANGER et al. (1977) with the SEQUENASE 2.0 version supplied by UNITED STATES BIOCHEMICAL CORP. The double strand DNA was sequenced according to the method described by JONES and SCHOFIELD (1990).

6) Segregation and link analysis

The link analysis with other labels was done using the link program developed by LANTHROP and et al. (1985). The data was obtained by segregation analysis in 40 families, supplied by a common panel of families from the Centre d'Etude du Polymorphisme Humain. Heterozygosity was established starting from grandparents or from parents if no grandparent was available.

7) In situ hybridization

Cytogenetic preparations have been obtained from lymphocytes. The DNA from cosmids (CEB) is marked by nick-translation using dUTP-11-digoxygenin (BOEHRINGER) as described by the manufacturer. The probe, with a final concentration of 1 to 3 μg/ml and the probed total human DNA at a final concentration of 200 to 300 μg/ml are denatured by heat (10 minutes in boiling water) and then placed in a hybridization buffer solution: 2×SSC, 20 nM Na$_2$HPO$_4$, 20nM Na$_2$H$_2$PO$_4$, 50% deionized formamide, 10% dextran sulfate, 0.1% SDS, 1% Denhart's solution.

After denaturation, 20 μl are used for each cytogenetic preparation plate. After addition of a plastic strip, the plates are incubated for 16 hours at 42° C. in a drying chamber. They are then washed twice in a 2×SSC buffer solution for 5 minutes at 42° C. The plates are then plunged for a duration of at least 10 min. in a PBS solution containing 0.1%, Tween 20, 1% BSA. After addition of 70 μl of an antibody, anti-FITC digoxigenin conjugated solution diluted to ⅛th the plates are incubated away from light for 45 minutes then rinsed in a PBS solution containing 0.1% Tween 20. Before observation, the plates are stained with 50 μl of propidium iodide solution at 0.3 μg/ml. The plates were photographed using Ektachrome 400 film and and a ZEISS II photomicroscope.

II - RESULTS

1) Isolation of polymorphic DNA sequences

G. VERGNAUD et al. (Electrophoresis 1991, 12, 134–140) showed that synthetic DNA probes formed of a short polymerized oligonucleotide detect polymorphic loci in the human genome. In order to study the possibility of identifying new polymorphic loci, the inventors explored a cosmid bank using polynucleotide probes 14C11, 14C21, 16C2, 16C4 and 16C27.

Southern blot analysis of the total human genomic DNA digested by conventional enzymes such as HinfI or HaeIII is shown in FIG. 1.

FIG. 1 represents the hybridization profile obtained with 6 non-consanguineous individuals using polynucleotides 14C11, 16C2 and 16C4 which were also used to explore the human cosmid bank. (In FIG. 1, the zone presented ranges from 0.5 to 10Kb.)

It appears that polynucleotides 14C11 and 16C2 detect a low number of bands whereas polynucleotide 16C4 shows a trail in the low molecular weight area (under 2 kb). Polynucleotides 14C21 and 16C27 detect a low number of bands.

In accordance with the prior results, the number of spots obtained after exploration of the 300,000 clones of the cosmid bank is on the order of 1,000 for polynucleotide 14C11, 250 for polynucleotide 16C2, 6000 for polynucleotide 16C4, 600 for polynucleotide 14C21 and 1500 for polynucleotide 16C27.

Among these, the Inventors have selected respectively 8, 10, 27, 10 and 11 cosmids giving the strongest signals. Different polymorphisms were thus identified in one of 8 cosmids selected which had reacted with polynucleotide 14C11, in 4 of the 10 cosmids selected which had reacted with polynucleotide 16C2, in 3 of the 27 cosmids selected which had reacted with polynucleotide 16C4, in 3 of the 10 cosmids selected which brad reacted with polynucleotide 14C21, in 8 of the 11 cosmids selected which had reacted with polynucleotide 16C27.

Two of the four polymorphisms identified with polynucleotide 16C2 were obtained twice. These were fragments of DNA CEB5 from cosmid 61 and fragment CEB3 from cosmid 66. In one of these cases, the cosmid inserts are different, as indicated by their restriction maps. This would suggest that two independent clones at the same locus are involved and that consequently polynucleotide 16C2 does not give access to a large number of loci in the human genome. In the other case, the cosmid inserts give the same restriction map with the HinfI enzyme. This is probably due to an amplified bank. Similarly, the ten clones detected by 14C21 correspond to 3 loci only, one obtained seven times, and another twice. Three of the eight loci isolated by 16C27 were obtained twice.

These results allow us to venture an estimate that the exploration of the cosmid bank using polynucleotides 14C11 and 14C4 has led to discovery of 3 to 5 times more polymorphic loci than by random exploration (Bowden et al., 1989). Better still, exploration with polynucleotide 16C2 led to discovery of about 20 times more polymorphic loci than by random exploration. Among the 10 cross-hybridizing clones with polynucleotide 16C2, 6 contain a highly polymorphic locus corresponding to 4 different polymorphic loci. Exploration with polynucleotide 14C21 led to discovery of 20 times more polymorphic loci than by random exploration and exploration with polynucleotide 16C27 led to discovery of about 30 times more polymorphic loci than by random exploration.

These results indicate that the most appropriate polynucleotides for exploration of a total genomic bank are those detecting a limited number of Southern blot bands without trail in the low molecular weight areas and a few tens to a few hundreds of colonies per equivalent genome.

Table 2 below lists the cosmid origin and size of the restriction fragments corresponding to the polymorphic DNA sequences as well as the polynucleotides which allowed their detection.

TABLE 2

| Fragment | Cosmid | Size (kb) | Restriction enzyme | Polynucleotide |
| --- | --- | --- | --- | --- |
| CEB1 | 53 | 3.8 | AluI | 16C2 |
| CEB2 | 54 | 6 | HinfI | 16C2 |
| CEB3 | 66 | 2.5 | HaeIII + HinfI | 16C2 |
| CEB4 | 83 | 3.8 | AluI | 14C11 |
| CEB5 | 61 | 3 | HaeIII | 16C2 |
| CEB13 | 101 | 4 | AluI + HaeIII | 14C21 |
| CEB15 | 102 | 3.8 | HinfI + HaeIII | 14C21 |

Figure 2:
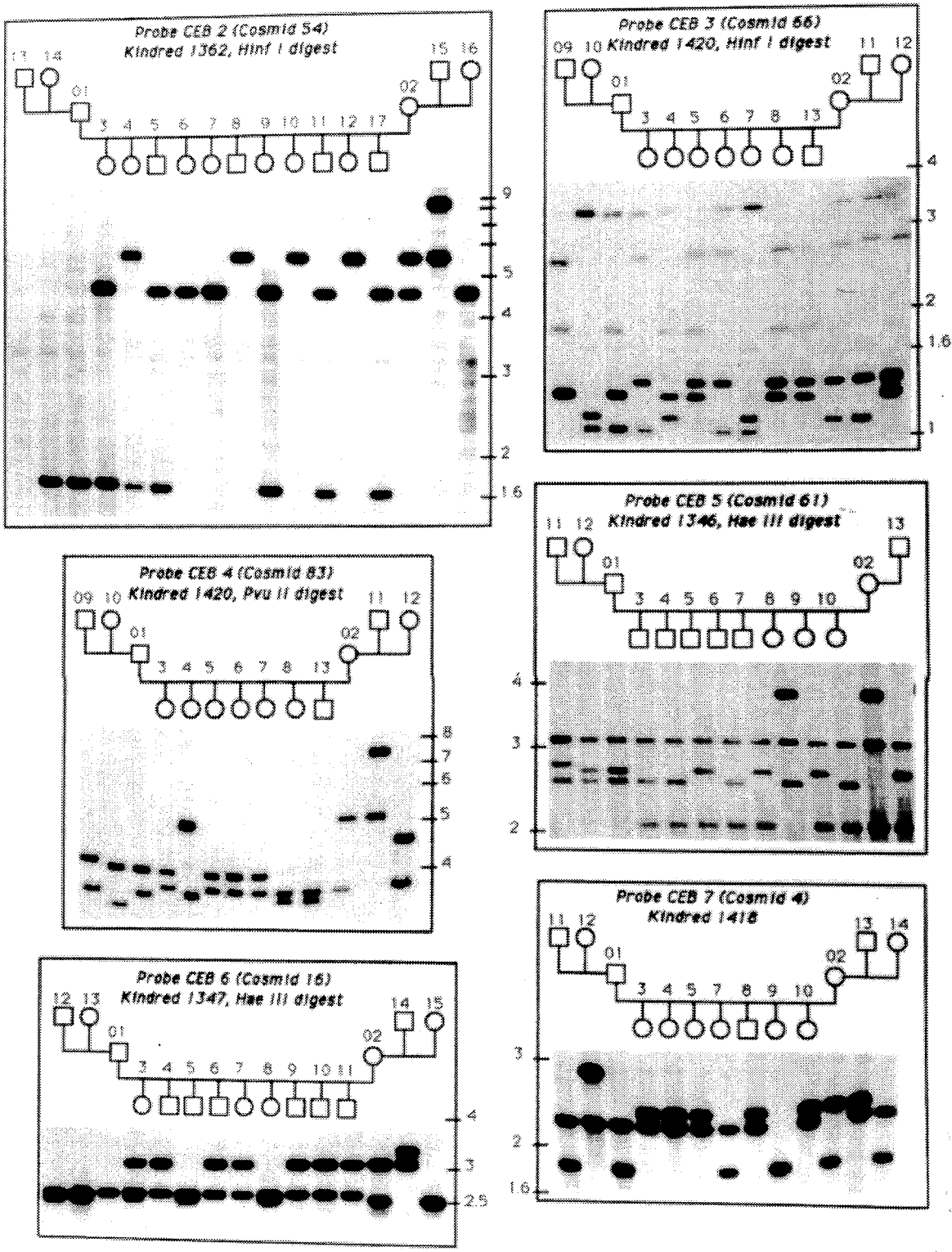
FIG. 2 shows the hybridization profiles of three generations of a common panel of formulas supplied by CEPH with fragments CEB2 from cosmid 54, CEB3 from cosmid 66, CEB4 from cosmid 83, CEB5 from cosmid 61, CEB6 from cosmid 16 and CEB7 from cosmid 4.
Figure 3A:
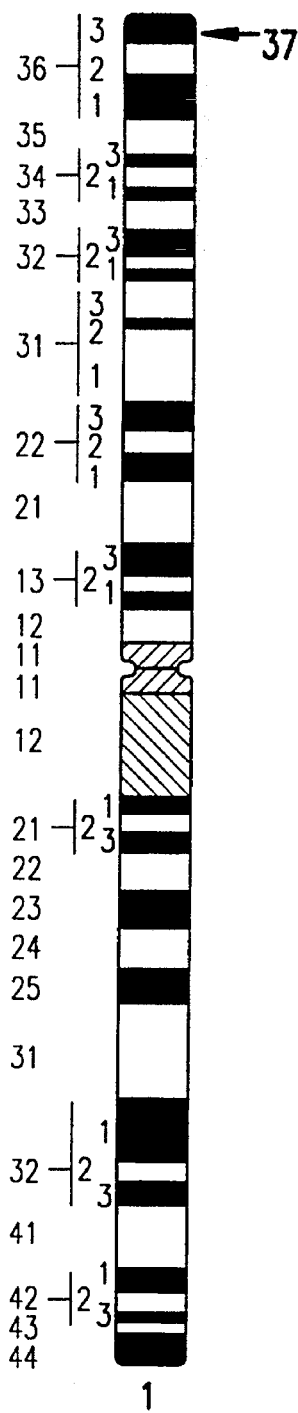
FIG. 3A–3H show the locations of cosmids 1, 2, 6, 8, 10, 11, 13 and 20, respectively the diagrams of human chromosomes.
Figure 3B:
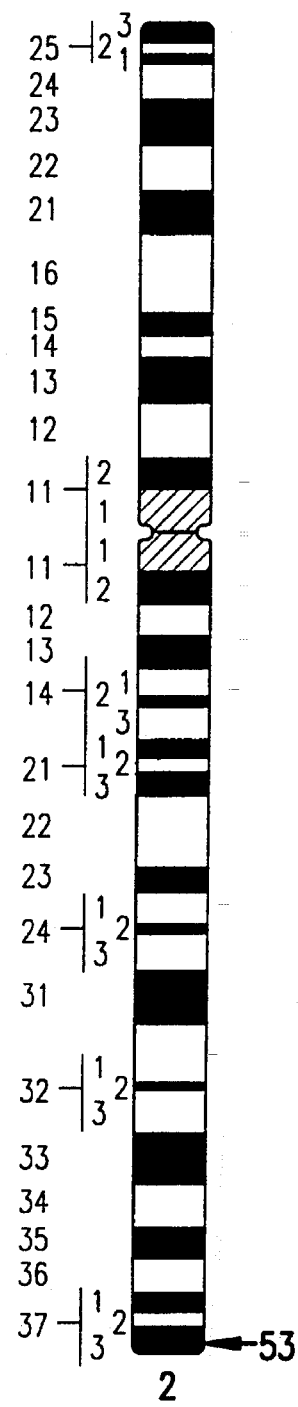
Figure 3C:
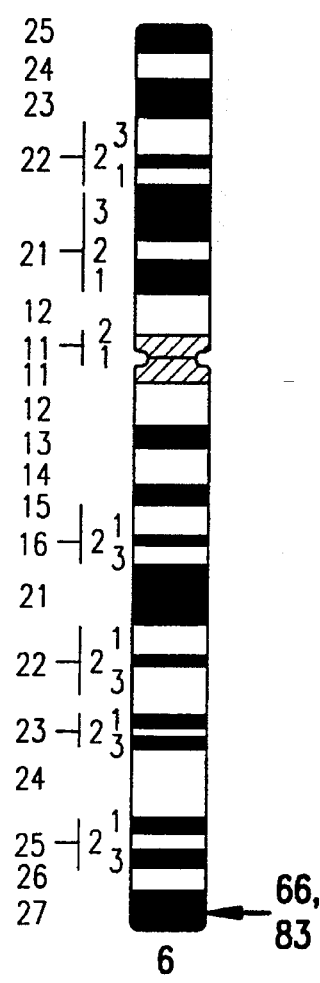
Figure 3D:
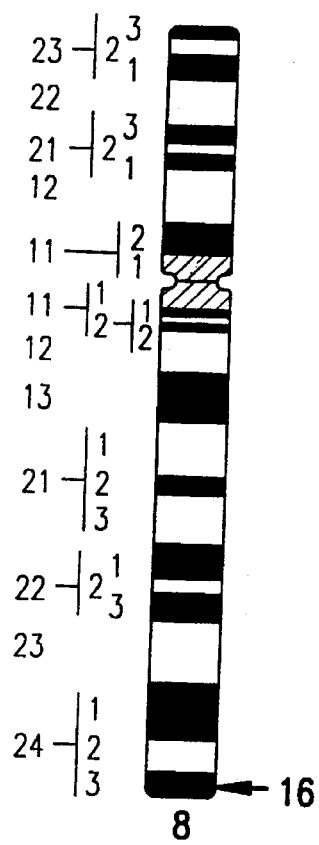
Figure 3E:
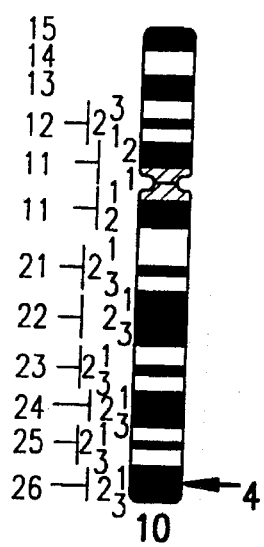
Figure 3F:
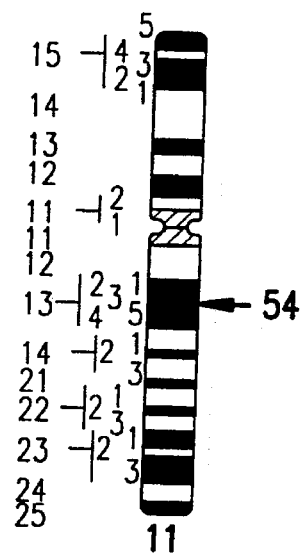
Figure 3G:
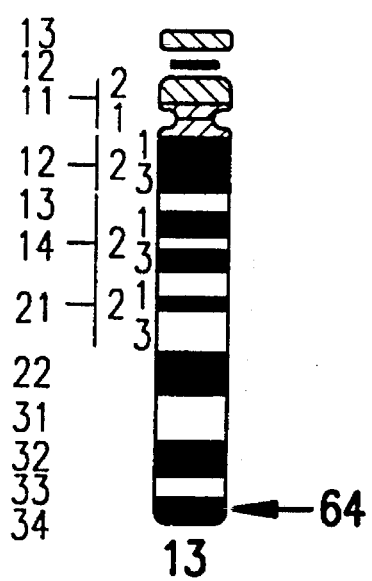
Figure 3H:
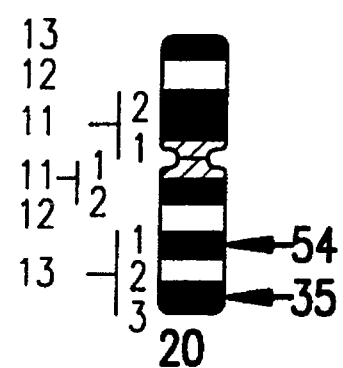

FIG. 2 represents the hybridization profiles, under high stringency conditions, of three generations of a common panel of families supplied by CEPH, with fragments CEB2 from cosmid 54, CEB3 from cosmid 66, CEB4 from cosmid 83, CEB5 from cosmid 61, CEB6 from cosmid 16 and CEB7 from cosmid 4. In FIG. 2, the squares represent men and the circles women. The number indicated over each square or circle corresponds to the identification number of the individual at CEPH. A scale on the side of the figure indicates the size in kilobases.

The bands detected in FIG. 2 do not belong to the fingerprint revealed by the polynucleotides.

The Inventors partially sequenced some of the isolated polymorphic loci.

In some cases, these inserts can be split by a restriction enzyme and the digestion fragments were also sequenced. In other cases, the inserts were sub-cloned in the pUC vector and the two ends were sequenced by double strand DNA sequencing. The 5 inserts studied contain tandem repeats.

The sequencing performed has allowed determining 3 DNA fragments forming a unitary motif with 2 to 500 tandem repeats, corresponding to new polymorphic loci. These are fragments CEB1 from cosmid 53, CEB2 from cosmid 54 and CEB5 from cosmid 61.

```
CEB1:
5' GTTGAGGGGGAGGGAGGGTGGTTGCGGAGGTCCCTGG 3' (SEQ ID NO: 6)
CEB2:
5' GAGGAGAGGGTGGCGGT 3' (SEQ ID NO: 7)
CEB5:
5' CTGTGCACCACCCAGGTCGAATCTCGGCTCACTGCGACCTC
TGCCTCCGCGTAG (SEQ ID NO: 8)
```

These results and the correlation observed by the Inventors between the size of the alleles and the intesity of the bands indicate that the polymorphism observed is really due to variations in the number of tandem repeats. The unitary motif repeated includes 7 to 8 bases in common with the synthetic oligonucleotide. In four cases, the Inventors noted that the unitary motif is rich in base G. Nevertheless, none of the sequences contains the consensus sequence GNNGTGGG defined by NAKAMURA et al. (1988).

2) Origin of the detection of cosmids not containing polymorphic loci with polynucleotide 16C4.

The Inventors sequenced the fragments hybridized with polynucleotide 16C4, from two cosmids among those which do not seem to detect polymorphic sequences in Southern blot and containing short sequences (TGGA) n (BOYLAND et al., 1990). A posteriori, this is not surprising since polynucleotide 16C4 is a multiple of 4 and contains twice the TGGA motif. Consequently, it appears that most of the clones detected by polynucleotide 16C4 corresponds to mini-satellites of this type. Thus only 3 (cosmids 4, 16 and 35) of the 27 clones, i.e. 10%, contain highly polymorphic loci (Fragment CEB10 from cosmid 37 is not highly polymorphic).

3) Chromosomic location by in situ hybridization

Table 3 below indicates the location by in situ hybridization of nine cosmids containing polymorphic loci. In Table 3:

Number D corresponds to the registering number attributed to the nucleotide sequence of the sub-fragment (CEB) by the GENOME DATA BASE (Baltimore, Md., USA).

"In situ" indicates the standard cytogenetic characteristic of the cosmid, i.e. its location on the chromosome with respect to the centromere.

"Allele size range" indicates the size of fragment detected by the polynucleotide in Southern, indicating the restriction enzyme used.

"Heterozygosity" indicates the number of heterozygotes for the allele considering 100 non-consanguineous individuals.

"Link with" indicates the name of a known close label whose number D is in brackets.

"Lod; Θ" indicates the genetic distance from this other label and the degree of certitude of this link.

CEPH and the regional attributions to the chromosomes have been obtained by analysis of the link with other labels already located (CEPH data base, version 3).

A cosmid (cosmid 35) detects two or more highly polymorphic loci under high stringency hybridization conditions and no location has been attempted for the polymorphic systems.

5) Study of a hypermutable locus: Probe CEB1 from cosmid 53

The CEPH families generally comprise three generations, grandparents, parents and children. Each individual is identified by a number composed of the family number followed by two digits. Fathers are 01 and mothers 02.

Table 4 below lists the mutations detected with the CEB1 sub-fragment. In Table 4:

51 children received no allele whose size corresponds to an allele from the father. One of them (1344 08) apparently has two abnormal alleles (aa). A "1" indicates that the individual has received the grandfather's allele for the second polymorphic locus corresponding to sub-fragment CEB11 from cosmid 53. A "2" has the same significance for the grandmother. This has not been determined (ND) when sub-fragment CEB11 is not instructive or when the grandparents are not available.

Size variation (+, −, m): the difference of size corresponds to the new allele smaller than the estimated size of the parental allele (m indicates the presence of an allele between the two parental alleles).

New size of allele: the sizes of the parental alleles are given only when the estimated size of the allele is unknown.

Recombination: indicates the state of recombination of the two ends of sub-fragment CEB1 (NI=not instruc-

TABLE 3

| Cosmid | D | Detected with polynucleotide | In situ | Sub-fragments | Size range of allele (Enzymes) | Hetero-zygosity (%) | Link with | Lod; θ |
| --- | --- | --- | --- | --- | --- | --- | --- | --- |
| 4 | D10S112 | 16C4 | 10q26.3 | CEB7 | 1,8–3 kb (HaeIII) | 50 | VTR4 (D10S6) | 31; 0.01 |
| 16 | D8S139 | 16C4 | 8q24.3 | CEB6 | 2.5–3.3 kb (HaeIII) | 38 | CHT16.8 (TG) | 4.5; 0.01 |
| 35 | | 16C4 | 20q13.3 | | | | | |
| 37 | D15153 | 16C4 | 1p36.3 | CEB10 | 1.8–2.7 kb (5 alleles) | 7 | CRI-L336 (D1547) | 6.2; 0.00 |
| 53 | D2S90 | 16C2 | 2q37.3 | CEB1 | <500 bp->12 kb (HinfI) | 93 | MCT106 (D2054) | 22; 0.00 |
| 54 | D20S33 | 16C2 | 20q13.1 | CEB2 | <500 bp->12 kb (HinfI) | 57 | MS1-27 (D20S4) | 27; 0.05 |
| 61 | D13S107 | 16C2 | 13q34 | CEB5 | 1.5–4 kb (HaeIII) | 80 | HT39 | 15; 0.08 |
| 66 | D6S132 | 16C2 | 6q27 | CEB3 | 500 bp–9 kb (HaeIII) | 95 | CRI-T22 (D6S25) | 9; 0.04 |
| 83 | D6S133 | 14C11 | 6q27 | CEB4 | 2.5–9 kb (PvuII) | 97 | CRI-T22 (D6S25) | 11; 0.04 |

Eight of nine cosmids containing polymorphic loci show a simple location. FIG. 3A–3H represent the locations of cosmids 1, 2, 6, 8, 10, 11, 13 and 20, respectively (indicated by an arrow in the figure) on the idiograms of human chromosomes. Cosmid 54, in all the metaphases observed, shows a major signal on band 20q13.1 and a weak signal on band 11q13.4.

4) Chromosomic location by link analysis

Link analysis is summed up in Table 2 above. Eight sub-fragments (CEB1 to CEB7 and CEB10) only detect a locus under high stringency hybridization conditions. This has been characterized in the common family panel from tive, ND: not determined). "Yes" indicates a recombination in the individual with the 33-CM area.

TABLE 4

| Individual | Parental allele lost | Size variation (bp) | New size of allele (kb) | Recombination |
| --- | --- | --- | --- | --- |
| 13291 04 | ND | + | 2.1 (1.3 & 2.0) | No |
| 13293 04 | 1 | +100 | 1.0 | No |
| 13293 06 | 1 | +300 | 1.7 | No |

TABLE 4-continued

| Individual | Parental allele lost | Size variation (bp) | New size of allele (kb) | Recombination |
|---|---|---|---|---|
| 13293 07 | 1 | −100 | 1.3 | No |
| 13294 04 | 1 | +100 | 2.0 | No |
| 13294 07 | 2 | +500 | 2.4 | ND |
| 1331 08 | 2 | −100 | 2.4 | No |
| 1331 17 | 2 | −100 | 2.4 | No |
| 1332 05 | 2 | +100 | 2.6 | No |
| 1332 06 | 2 | +300 | 1.8 | No |
| 1333 03 | ND | m | 2.9 (1.5 & 3.0) | No |
| 1333 05 | ND | + | 3.3 (1.5 & 3.0) | No |
| 1334 05 | 2 | +200 | 4.6 | NI |
| 1334 08 | 1 | −200 | 2.4 | NI |
| 1340 03 | 2 | −100 | 2.2 | Yes |
| 1340 05 | 2 | +100 | 2.4 | Yes |
| 1341 02 | ND | + | 2.7 (2.0 & 2.6) | NI |
| 1341 04 | 1 | −100 | 2.3 | NI |
| 1341 08 | 1 | +100 | 2.5 | NI |
| 1341 09 | 2 | −100 | 2.6 | NI |
| 1344 03 | ND | m | 2.6 (1.7 & 2.7) | NI |
| 1344 08 | 2 aa | | 1.8 & 3.4 | NI |
| 1346 06 | ND | m | 4.9 (4.8 & 5) | ND |
| 1346 07 | ND | + | 5.1 (4.8 & 5) | ND |
| 1346 09 | ND | m | 4.9 (4.8 & 5) | ND |
| 1349 03 | 2 | −1800 | 400 bp | No |
| 1349 06 | 1 | +200 | 2.1 | No |
| 1350 04 | 1 | +100 | 5.1 | ND |
| 1350 05 | 1 | −500 | 4.4 | No |
| 1350 06 | 1 | +100 | 5.1 | ND |
| 1362 10 | ND | m | 2.1 (2.0 & 2.2) | Yes |
| 1362 12 | ND | + | 2.8 (2.0 & 2.2) | Yes |
| 1377 01 | ND | + | 2.1 (1.7 & 1.9) | ND |
| 1377 02 | ND | m | 3.2 (2.5 & 3.5) | ND |
| 1408 09 | 1 | −100 | 3.2 | No |
| 1413 04 | 2 | +100 | 3.7 | No |
| 1413 16 | 2 | −100 | 3.5 | Yes |
| 1420 13 | 2 | +500 | 2.9 | No |
| 1423 04 | 1 | −100 | 3.0 | No |
| 1424 10 | ND | m | 1.1 (1.0 & 4.3) | No |
| 66 08 | 2 | +600 | 2.6 | NI |
| 12 05 | ND | m | 3.5 (1.1 & 4.8) | No |
| 12 06 | ND | + | 4.9 (1.1 & 4.8) | No |
| 02 04 | ND | + | 3.5 (2.2 & 3.2) | Yes |
| 17 06 | ND | + | 4.0 (0.9 & 3.7) | NI |
| 17 07 | ND | + | 3.9 (0.9 & 3.7) | NI |
| 17 08 | ND | m | 3.5 (0.9 & 3.7) | NI |
| 35 05 | ND | + | 5.8 (2.5 & 5.6) | ND |
| 884 05 | 1 | +200 | 2.2 | Yes |
| 102 08 | ND | m | 1.2 (0.4 & 1.3) | Yes |
| 104 04 | ND | + | 3.9 (1.8 & 3.8) | ND |
| 104 06 | ND | m | 3.5 (1.8 & 3.8) | ND |
| 104 08 | ND | + | 3.9 (1.8 & 3.8) | ND |

Figure 4:
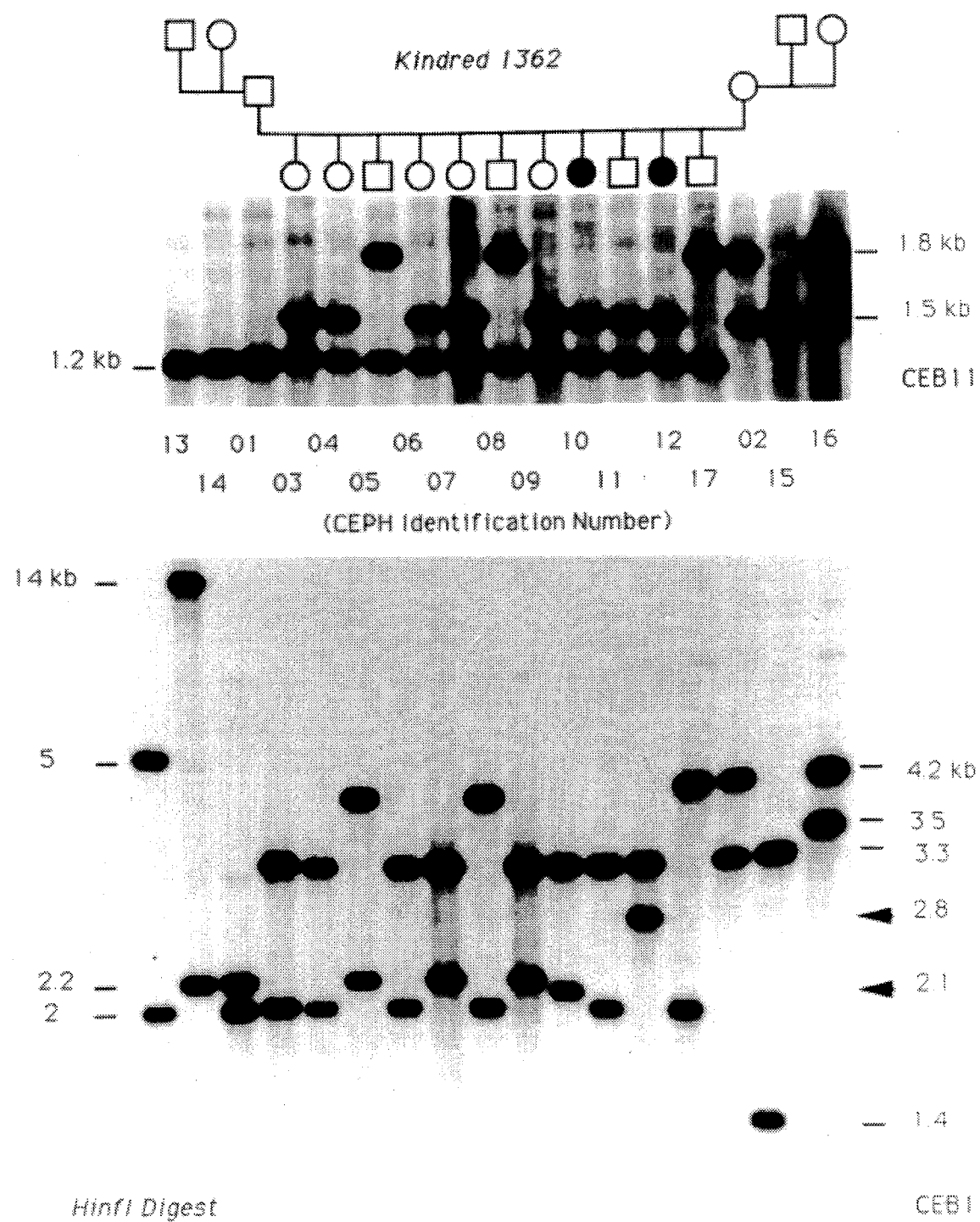
FIG. 4 shows hybridization profiles of three generations of a common panel of families provided by CEPH with cosmid fragments CEB1 and CEB11 from cosmid 53 as probes and using restriction enzymes HinfI.

FIG. 4 represents hybridization profiles, under high stringency conditions, of three generations of a common panel of families provided by GEPH, with cosmid fragments CEB31 and CEB11 from cosmid 53 as probes and using restriction enzyme HinfI. In FIG. 4, the squares represent men and the circles women. The numbers are the CEPH identification numbers. Black circles indicate individuals with a new allele (arrow). In the example of FIG. 4, CEB11 is homozygotous with the father. Consequently, the origin of the adjacent region determined by CEB11 cannot be identified with the grandparents.

The characterization of CEB1 in the panel supplied by CEPH reveals the presence of neo-mutations (presence of an allele absent in the parents) with 51 of the 310 children studied and with 3 parents. Sampling errors can be excluded as source of contradiction since 5 other sequences detecting highly polymorphic loci were used as probes on the same membrane. Besides, with all the mutations except one, the abnormal allele came from the father. Such a paternal source cannot have been caused by sampling errors.

Cosmid 53 from which CEB1 is drawn, was localized by in situ hybridization at the level of band 37 of the arm of chromosome 2 q. The link analysis using sub-fragment CEB1 shows that the region involved contains five RFLP labels in 33 cM (men) (O'CONNELL et al., 1989). When the whole of cosmid 53 is used as probe in Southern, more than two additional bands appear under the same hybridization conditions. This indicates the existence of another polymorphic locus, corresponding to sub-fragment CEB11. No recombination was observed between CEB11 and CEB1, the latter being separated by less than 40 kb. No neo mutation was observed with CEB11 in the panel of families provided by CEPH. In the families for which CEB11 is instructive and for which a mutation appears on CEB1, the grandparental origin of the mutated allele can be determined (as indicated in Table 4).

The mutations in the alleles transmitted by the grandfather and grandmother have been observed in a single family (family 13291) and in two families (families 13291 and 13293) with the same paternal grandparents. An equal frequency of mutations was observed for all the alleles from the paternal grandfather and grandmother. Table 4 sums up the results observed concerning the grandparental origin of the allele involved in 51 cases of mutation and also provides an estimation of the difference between the expected size and the observed size of the alleles.

FIG. 5 represents the distribution in size of the HinfI alleles observed with the CEB1 fragment. In this distribution, the size of the alleles observed in the grandparents of the panel supplied by CEPH and that of the alleles of the parents without accessible parent have been estimated. Similarly, when only one band has been displayed and transmitted, the individual has been considered as homozygotous and the allele counted twice. This leads to sub-estimating the number of small alleles.

The mutations at the locus detected by fragment CEB1 does not seem to correlate to a large sized allele. However, it would seem that there is a correlation between the increase in size of the allele and the cases of mutation. In reality, for 30 mutations, the size of the allele increased whereas the size decreased for 12 mutations. For 12 mutations, the variations in size are unknown since the origin of the allele could not be determined and the size of the new allele is between the sizes of the two parental alleles.

The analysis of multilocus links with respect to other genetic labels reported for this region by O'CONNEL et al. (1989) helped to determine the following layout: 5.1.25- MCOE32- (MCT106- CEB1) - EKZ105- YNA4. No recombination was observed between the loci detected by CEB1 and MCT106.

As indicated in Table 4, recombinations between the instructive adjacent labels could be determined in 29 of the meiosis involved in neo-mutations at the loci detected by CEB1. Recombinations were observed in only 8 cases. This is the same as the frequency of cases of recombination observed in meioses without apparent mutation. Consequently it would not seem that the mutations detected by fragment CEB1 are associated with unequal crossings over.

III - DISCUSSION

The study performed is a striking example of the possibility of using unspecified oligonucleotide polymers in tandem repeats to identify new polymorphic loci. The success of such an identification is correlated to the number of highly positive clones obtained during the exploration of the bank. Polynucleotide 16C2 allowed identification of about 60 clones by equivalent genome and 6 to 10 cosmids tested detected polymorphisms corresponding to 4 different polymorphic loci. On the contrary, polynucleotides 14C11 and 16C4 allowed detecting a large number of clones, respectively about 250 and 1500 cosmids per equivalent genome, and only one polymorphic locus was found out of the 8 clones tested after selection with polynucleotide 14C11. With polynucleotide 16C4, 3 of the 27 clones which were tested allowed detection of polymorphisms. These results indicate that the efficiency of the selection could be increased by using only polynucleotides which detect only a few tens of colonies per equivalent genome. This is not a limitation to the process for detection of polymorphic loci according to the invention since a large number of polynucleotides can be tested and a given mini-satellite region can be detected independently by different polynucleotides.

About 200 polymorphic loci have been detected to date by exploring cosmid banks with oligonucleotides enriched in Guanine, identical to the isolated repetitive motifs of mini-satellite sequences isolated previously (NAKAMURA et al. 1987, 1988). The minimum number of such loci in the human genome is estimated at 1500. New techniques allowing for detection of new polymorphic loci are necessary for genetic mapping.

The invention process can be compared to the use of cloned VNTR probes detecting nearby VNTR families. The main difference lies in the unlimited number of new polynucleotides and in the fact that some of them detect by hybridization, in low stringency conditions, a small number of cosmids a high proportion of which contain a polymorphic locus. Inversely, when a limited number of multilocus probes are available, when these probes detect numerous loci in the human genome (ROYLE et al. 1988), it can be necessary to build a special bank rich in mini-satellite sequences to draw cross - hybridizing monomorphic fragments with the probe in order to obtain a higher efficiency in identifying polymorphic loci. The procedure generally used consists in cloning large-size fragments, after digestion by restriction enzymes such as Sau3A (Mbol), HaeIII (WONG et al., 1987; ARMOUR et al., 1990, GEORGES et al., 1991). A consequence could be that mini-satellites with a predominance of small alleles are difficult to obtain.

The results of the study reported in the context of a description of the invention confirm that VNTRs are grouped in telomeric regions of the human genome. It is thus interesting to note that the new polymorphic loci detected in the context of the invention have a distribution similar to that of the VNTRs already identified.

The polynucleotides used with man in the invention process are also usable for numerous species such as mice, rats, bovines, dogs and horses.

Concerning the probes of the invention, one of them detects a locus which appears highly mutable. Although the DNA used in this study comes from cellular lines of transformed lymphoblasts, it is highly unlikely that the mutations took place during the culture of the cells (ARMOUR et al., 1989). This invention affords direct evidence for the existence in man of a highly mutable polymorphic locus (CEB1) which mutation takes place mainly in male meiosis. Evidence for a locus with different mutation rates for man and woman provides an encouraging clue to search for other highly mutable loci. The location of these loci will allow mapping of the human genome correlated with other observations concerning, for example, different rates of recombination for man and for woman.

On the contrary, no mutation was observed with the CEB11 probe, corresponding to a polymorphic locus detected on the same cosmid as CEB1. The nucleotide sequences of CEB1 and MS1 (65% GC; 5G-1C) are extremely rich in Guanine and Cytosine and contain a strand rich in Guanine. Numerous other VNTR loci show the same distribution without high mutation rates. The mutations detected by CEB1 are not related to the sizes of the allele as shown in Table 4 and FIG. 5. However, there seems to be a correlation between the increase in size of the allele and the cases of mutation. The isolation of hypermutable sites is also important to understand the nature of the rearrangements taking place m the generation of the variability of the VNTR locus. The hypothesis according to which the new alleles are generated by an unequal exchange between homologous regions has already been studied for three loci. A simple mutation of maternal origin at locus D17S5 has been characterized at the molecular level by WOLFF and al. (1988) and 36 mutations have been observed in the CEPH panel at locus D1S7 (MS1). The genetic analysis with significant adjacent RFLPs was applied to 12 mutations with the purpose of detecting cases of crossing-over (WOLFF et al., 1989). The D1S8 locus (MS32) was studied while mapping the internal variations of more than 60 meiotic mutants (JEFFREYS et al., 1990). In all cases, it appears that the new alleles are not generated by unequal crossings-over.

Preliminary data reported in this study strongly suggest that the mutations at the level of the locus detected by the CEB1 nucleotide sequence are also not generated by an unequal exchange between homologous sections. Twenty-nine cases of mutation occurred in individuals, doubly significant for adjacent labels m a 33-CM region, and only 8 individuals show recombination in the region. Consequently, the question of the origin of the additional DNA in the allele, whose size has increased because of mutations, remains unsolved. The mapping of internal variations as described by JEFFREYS et al. (A990) applied to polymorphic loci defined by CEB1 could be a promising approach to answer this question.

BIOGRAPHICAL REFERENCES

1. ARMOUR, J. A. L., PATEL, I., THEIN, S. L., FEY, M. F.,AND JEFFREYS, A. J. (1989) Genomics 4: 328–334.
2. ARMOUR, J. A. L., POVEY, S., JEREMIAH, S., AND JEFFERYS, A. J. (1990) Genomics 8: 501–512.
3. BLONDEN, L. A. J., DEN DUNNEN, J. T., VAN PASSEN, H. M. B., WAPENAAR, M. C., GROOTSCHOLTEN, P. M., GINJAAR, F. B., BAKKER, E., PEARSON, P. L., AND VAN OMMEN, G. J. B. (1989), Nucleic Acids Res. 17: 5611–5621.
4. BOWDEN, D. W., MüLLER-KAHLE, H;, GRAVIUS, T. C. HELMS, C., WATT-MORGAN, D., GREEN, P., AND DONIS-KELLER, H. (1989), Am. J. Hum. Genet. 44: 671–678.
5. BOYLAN, K. B., AYRES, T. M., POPKKO, B., TAKAHASHI, N., HOOD, L. E., AND PRUSINER, S. B. (1990), Genomics 6: 16–22.
6. FEINBERG, A. P., AND VOGELSTEIN, B. 1983, Anal. Blochem. 132: 6–13.
7. GEORGES, M., GUNAWARDANA, A., THREADGILL, D., LATHROP, M., OLSAKER, I., MISHRA, A., SARGEANT, L., STEELE, M., TERRY, C., ZHAO, X., HOLM, T., FRIES, T., AND WOMACK, J. (1991), Proc. Natl. Acad. Sci. USA, in press.
8. GEORGES, M., LATHROP, M., HILBERT, P., MARCOTTE, A., SCHWERS, A., SWILLENS, S., VASSART, G., AND HANSET, R. (1990), Genomics 6: 461–474.
9. GOODBOURN, S. E. Y., HIGGS, D. R., CLEGG, J. B., AND WEATHERALL, D. J. (1983) Proc. Natl. Acad. Sci. USA 80: 5022–5026.

10. JEFFREYS, A. J. (1987) *Biochem. Soc. Trans.* 15: 309–317.
11. JEFFREYS, A. J., NEUMANN, R., AND WILSON, V. (1990) *Cell.* 60: 473–485.
12. JEFFREYS, A. J., ROYLE, N. J., WILSON, V., AND WONG, Z. (1988) *Nature* 332:278–281.
13. JEFFREYS, A. J., WILSON V., KELLY, R., TAYLOR, B. A., AND BULFIELD, G. (1987). *Nucleic Acids Res.* 15: 2823–2836.
14. JONES, D. S. C., AND SCHOFIELD, J. P. (1990) *Nucleic Acids Res.* 18: 7463–7464.
15. JULIER, C., DE GOUYON, B., GEORGES, M., GUENET, J. L., NAKAMURA, Y. AVNER, P., AND LATHROP, G. M. (1990) *Proc. Nacl. Acad. Sci. USA* 87: 4585–4589.
16. KELLY, R., BULFIELD, G., COLLICK, A., GIBBS, M., AND JEFFREY5, A.J. (1989) *Genomics* 5: 844–856.
17. LATHROP, G. M., LALOUEL, J. M., JULIER, C., AND OTT, J. (1985) *Am. J. Hum. Genet.* 37: 482–498.
18. NAKAMURA, Y., CARLSON, M., KRAPCHO, K., KANAMORI, H., AND WHITE, R. (1988) *Am. J. Hum. Genet.* 43: 854–859.
19. NAKAMURA, Y., LATHROP, M., O'CONNEL, P., LEPPERT, M., KAMBOH, M. I., LALOUEL, J. M., AND WHITE, R. (1989) *Genomics* 4: 76–81.
20. NAKAMURA, Y., LEPPERT, M., O'CONNEL, P., WOLLF, R., HOLM, T., CULVER, M., MARTEN, C., FUJIMOTO, E., HOFF, M., KUMLIN, E., AND WHITE, R. (1987) Science 235: 1616–1622.
21. NÜRNBERG, P., ROEWER, L., NEITZEL, H., SPERLING, K., PÖPPERL, A., HUNDRIESER, J., PÖCHE, H., EPPLEN, C., ZISCHLER, H., AND EPPLEN, J. T. (1989) Hum. Genet. 84: 75–78.
22. O'CONNEL, P., LATHROP, M., NAKAMURA, Y., LEPPERT, M. L., LALOUEL, J. M., AND WHITE, R. (1989) *Genomics* 5: 738–745.
23. A. J., ROYLE, CLARKSON, R. E., WONG, Z;, AND JEFFREYS, A. J. (1988) *Genomics* 3: 352–360.
24. SAMBROOK, J., FRITSCH, E. F., AND MANIATIS, T. (1989) Cold Spring Harbor Laboratory Press, Cold Spring Harbor, N.Y.
25. SANGER, F., NICKLEN, S., AND COULSON, A. R. (1977) *Proc. Natl. Acad. Sci. USA* 77: 5463–5467.
26. VERGNAUD, G. (1989) *Nucleic Acids Res.* 17: 7623–7630.
27. VERGNAUD, G., MARIAT, D., ZOROASTRO, M., AND LAUTHIER, V. (1991) *Electrophoresis* 12: 134–140.
28. WOLFF, R., NAKAMURA, Y., AND WHITE, R. (1988) *Genomics* 3: 347–351.
29. WOLFF, R. K., PLAETKE, R., JEFFHEYS, A. J., AND WHITE, R. (1989) *Genomics* 5: 382–384.
30. WONG, Z., WILSON, V., PATEL, I., POVEY, S., AND JEFFREYS, A. J. (1987) *Ann. Hum. Genet.* 51: 269–288.

---

I claim:

1. A polynucleotide according to the following formula: $(ACGGAGCGGACGGA)_n$ (SEQ ID No: 2), wherein n is higher than 20.

2. A polynucleotide according to the following formula: $(AGCTACGGTGTGGACT)_n$ (SEQ ID No: 5), wherein n is higher than 20.

3. An isolated and purified polynucleotide for identifying polymorphic loci by hybridization, said polynucleotide consisting of a 4kb Alu1-HaeIII human genomic DNA insert present in cosmic clone CEB13 deposited at CNCM under accession No I-1135.

4. An isolated and purified polynucleotide for identifying polymorphic loci by hybridization, said polynucleotide consisting of a 3.8 kb HinfI-HaeIII human genomic DNA insert present in cosmic clone CEB15 deposited at CNCM under accession No. I-1136.

* * * * *